US008554087B2

(12) United States Patent
Osterberg

(10) Patent No.: US 8,554,087 B2
(45) Date of Patent: Oct. 8, 2013

(54) SYSTEM AND METHOD FOR IMAGING OBJECTS THROUGH TURBID MEDIA

(75) Inventor: Ulf Osterberg, Etna, NH (US)

(73) Assignee: The Trustees of Dartmouth College, Hanover, NH (US)

(*) Notice: Subject to any disclaimer, the term of this patent is extended or adjusted under 35 U.S.C. 154(b) by 1065 days.

(21) Appl. No.: 12/441,859

(22) PCT Filed: Sep. 14, 2007

(86) PCT No.: PCT/US2007/078503
§ 371 (c)(1),
(2), (4) Date: Sep. 8, 2009

(87) PCT Pub. No.: WO2008/036567
PCT Pub. Date: Mar. 27, 2008

(65) Prior Publication Data
US 2010/0021177 A1 Jan. 28, 2010

Related U.S. Application Data

(60) Provisional application No. 60/845,469, filed on Sep. 18, 2006.

(51) Int. Cl.
*H04B 10/04* (2011.01)
*H04B 10/12* (2011.01)

(52) U.S. Cl.
USPC ........... 398/199; 398/189; 398/195; 250/340; 250/341.1; 372/20; 372/28; 372/32

(58) Field of Classification Search
USPC .................. 356/342; 372/25, 29.011, 30, 32, 372/20, 28; 398/118–131, 182–201; 250/330–334, 241.8, 339.11, 340, 341.1
See application file for complete search history.

(56) References Cited

U.S. PATENT DOCUMENTS 6,091,356 A * 7/2000 Sanders et al. ................ 342/132
6,495,833 B1 * 12/2002 Alfano et al. ............... 250/341.8
(Continued)

FOREIGN PATENT DOCUMENTS

WO 9719632 A 6/1997
WO 2006045936 A 5/2006

OTHER PUBLICATIONS

Hee, M.R. "Femtosecond Transillumination Tomography in Thick Tissues," Optics Letters, OSA, Optical Society of America, Washing, DC, US, vol. 18, No. 13, Jul. 1, 1993, p. 1107.
(Continued)

*Primary Examiner* — Danny Leung
*Assistant Examiner* — Daniel Dobson
(74) *Attorney, Agent, or Firm* — Lathrop & Gage LLP

(57) ABSTRACT

A method for imaging objects through turbid media includes generating a repetitive pulsed light beam under control of a pulse shaper, propagating the light beam through turbid media, and receiving and imaging the light beam at a sensor. Propagation through turbid media causes scattering of the light, and the sensor captures scattered pulses to produce an image. The pulse shaper controls pulse width, frequency, repetition rate and chirp of the generated light pulses according to a feedback signal received from the sensor, to improve image quality. A system for imaging objects through turbid media includes a laser for generating a light beam; a pulse shaper for controlling said light beam, and a sensor, in communication with the pulse shaper, for capturing the image of said light beam through a turbid medium. Pulse width is less than 250 femtoseconds to reduce attenuation of the light beam through the turbid medium.

14 Claims, 4 Drawing Sheets

(56) References Cited

U.S. PATENT DOCUMENTS

| | | | |
|---|---|---|---|
| 2003/0048499 A1* | 3/2003 | Alfano et al. | 359/110 |
| 2004/0059225 A1* | 3/2004 | Hao et al. | 600/458 |
| 2005/0018984 A1* | 1/2005 | Carbone et al. | 385/123 |
| 2005/0226287 A1* | 10/2005 | Shah et al. | 372/25 |
| 2007/0147847 A1* | 6/2007 | Zheng et al. | 398/158 |
| 2009/0240148 A1* | 9/2009 | Jeong et al. | 600/439 |

OTHER PUBLICATIONS

Abraham, E., et al, "Real-Time Two-Dimensional Imaging in Scattering Media by Use of a Femtosecond Cr4+: Forsterite Laser," Optics Letters, OSA, Optical Society of America, Washing, DC, US, vol. 25, No. 12, Jun. 15, 2000, pp. 929-931.

Papazoglou, T.G., et al. "Effect of Diffraction on Early-Arriving Photons During Femtosecond Laser Transillumination of Highly Scattering Media of Biological Significance," Applied Optics, OSA, Optical Society of America, Washington, DC, US, vol. 35, No. 19, Jul. 1, 1996, pp. 3759-3762.

Hyde, S.C.W., et al. "High Resolution Depth Resolved Imaging Through Scattering Media Using Time Resolved Holography," Optics Communications, North-Holland Publishing Col, Amsterdam, NL, vol. 122, No. 4, Jan. 1996, pp. 111-116.

Delfino, I., et al., "Random Walk Analysis of Time-Resolved Transmittance Measurements," Proceedings of the SPIE, SPIE, Bellingham, VA, US, vol. 4955, No. 1, Jan. 26, 2003, pp. 536-545.

Alrubaiee, M., et al. "Time-Resolved and Quasi-Continuous Wave Three-Dimensional Tomographic Imaging of Objects in Tissue-Like Turbid Media," Proceedings of the SPIE, SPIE, Bellingham, VA, US, vol. 5463, No. 1, Apr. 29, 2004, pp. 82-85.

Papazoglou, T.G., "Interactions of Ultrafast Laser Pulses With Biologic Tissues," Proceedings of the SPIE, SPIE, Bellingham, VA, US, vol. 4001, Oct. 5, 1999, pp: 102-113.

Baigar, E., et al., "Imaging Within Highly Scattering Media Using Time-Resolved Backscattering of Femtosecond Pulses," Applied Physics B: Lasers and Optics, Springer International, Berlin, DE, vol. B67, No. 2, Aug. 1998, pp. 257-261.

Mujumdar, S., et al., "Few-Cycle Pulse Propagation in Multiple Scattering Media," Optics Communications, North-Holland Publishing Co., Amsterdam, NL, vol. 247, No. 1-3, Mar. 1, 2005, pp. 19-27.

Brixner, T., et al., "Feedback-Controlled Femtosecond Pulse Shaping," Applied Physics B, Lasers and Optics, Springer, Berlin, DE, vol. B70, Jun. 2000, pp. S119-S124.

International Search Report and Written Opinion issued in related PCT Patent Application Serial No. PCT/US2007/078503, Jun. 25, 2008, 19 pages.

* cited by examiner

000
SYSTEM AND METHOD FOR IMAGING OBJECTS THROUGH TURBID MEDIA

RELATED APPLICATIONS

The present application claims priority from U.S. provisional patent application No. 60/845,469 entitled "System and Method for Imaging Object Through Turbid Media", filed 18 Sep. 2006, the disclosure of which is incorporated by reference herein.

U.S. GOVERNMENT RIGHTS

This invention was made in part with the support of the U.S. Government; the U.S. Government has certain rights in this invention as provided for by the terms of Grant #60NANB4D1142 awarded by the National Institute for Science and Technology.

FIELD OF THE INVENTION

The present document relates to the fields of optical imaging and communicating through turbid media.

BACKGROUND OF THE INVENTION

Imaging through turbid media has many diverse applications within aviation, defense, astrophysics, marine science, biology and medicine, etc. For example, imaging cars, ships and troops through fog, aircraft through clouds, body parts and foreign objects through human or animal blood and/or tissue or clothing, viewing through filled or fiber-reinforced plastics, or searching for objects in murky water are all applications where it may be desirable to improve visibility through turbid media. It is also often desirable to communicate through turbid media such as fog or seawater.

The turbid medium typically has at least two components, a first or base medium component having a first set of optical properties, and a second or scattering-particle component having a second set of optical properties. When photons pass through the turbid medium, they may pass through the base medium component between the scattering particles, and not be affected by the scattering particles; these photons are the ballistic photons. Alternatively, photons may pass through the base medium component until they are affected by a particle of the scattering particle component. These photons may then be deflected or reflected through a distribution of wide and narrow deflection angles by their interaction with the scattering particles, the distribution of deflection angles will vary according to the wavelength of the photons, the particle size of the particles, and optical properties of the base medium component and the scattering particle component. Photons may undergo multiple interactions with scattering particles, as well as an object of interest.

The mean free path Is represents the average distance a photon may travel in the medium before being scattered. The ballistic, or unscattered, photons have intensity $I=Io\exp(-x/l^*_s)$ where Io is the input intensity, and x is the distance traveled. Snake photons are those that have been deflected by one or more scattering particles in a more-or-less forward direction, hence emerge from the media with small delay relative to the ballistic photons. Diffusive photons have been deflected many times or have been deflected through wide angles, hence emerging with longer delay and forming an incoherent background that can obscure objects of interest located within the medium.

Some turbid media, such as human and animal tissue, are considerably more complex than the above description, and may include a wide range of scattering particles and, at times it may be difficult to determine even what is base medium and what is scattering particles. Photons penetrating such media will, however, still become divided into populations of ballistic, snake, and diffusive photon components and, as the diffusive component becomes large relative to the ballistic component, vision through the media may be badly impaired.

Inhomogeneities in a medium, such as scattering particles, cause scattering which may alter the direction of propagation, polarization and phase of photons passing through the medium. The amount of light passing through the turbid medium may also be significantly reduced by absorption and scattering at particles within the medium. The net effect of the Inhomogeneities is to render many objects difficult to view without assistance.

When an object of interest, such as a road sign, car, vehicle, soldier, ship, bone, bullet, tumor, or other object is present within a turbid medium, the object of interest is illuminated by a combination of the ballistic, snake, and diffusive photons. These illumination photons interact with the object, and some of them being absorbed by the object and some of them are reflected by the object. Photons reflected by the object may in turn become divided into populations of ballistic, snake, and diffusive photons enroute to any imaging system observing the diffusive medium.

Prior systems for imaging in turbid media have attempted to separate diffusive from ballistic photons based upon the time of arrival of these photons at a sensor. Because transit time of ballistic photons must be known to set an acceptance window, these systems tend to work better with shadow imaging, requiring a sensor on an opposite side of the turbid medium from a light source; and do not work well with light reflected by an object of interest in the medium, where the transit time may not be known.

SUMMARY

A method for imaging objects through turbid media includes generating a repetitive pulsed light beam under control of a pulse shaper. The light beam is propagated through turbid medium, received at a sensor and imaged.

A software product for modifying laser pulses includes instructions, stored on computer-readable media. When executed by a computer controlling a laser and coupled to a sensor, the instructions perform steps for modification of laser pulses, including: analyzing output of the sensor to determine an optimum value for one or more of pulse width, frequency, repetition rate and chirp of laser pulses emitted by the laser; and adjusting the laser pulse width, frequency, repetition rate or chirp based on the optimum values.

A system for imaging objects through turbid media includes a laser for generating a light beam; a pulse shaper for controlling said light beam, and a sensor, in communication with the pulse shaper, for capturing the image of said light beam through a turbid medium.

DETAILED DESCRIPTION OF THE EMBODIMENTS

A chirp is a signal in which the frequency increases ('up-chirp') or decreases ('down-chirp') with time. Chirps are commonly used in sonar and radar, but have other applications, such as in spread spectrum communications. In optics, ultrashort laser pulses exhibit chirp due to rapid changes in operating parameters as each pulse is generated and the dispersion and non-linearities of the materials they propagate through.

Chirp modulation, or linear frequency modulation for digital communication was originally introduced by Winkler in 1962. This type of modulation employs sinusoidal waveforms whose instantaneous frequency increases or decreases over time. These waveforms are commonly referred to as chirps. The rate at which their frequency changes is called the chirp rate.

A laser may be configured to generate very short pulses (e.g., a duration between 5-500 femtoseconds) of visible or infrared light at a certain wavelength (e.g., 300 nm-3 µm) with a certain repetition rate (e.g., single pulse—100 MHz) and a certain chirp. There are tunable lasers available that permit electronic setting and adjustment of one or more of these parameters over a range supportable by the particular laser.

By varying the pulse wavelength, pulse width, repetition rate and/or chirp until reduced (relative to ordinary light) absorption of the light within the turbid media is experienced, propagation of light through the turbid media may be improved, thereby improving imaging of objects within the turbid media.

In particular, it has been found experimentally that use of laser pulse widths narrower than a dielectric relaxation time of the medium causes unexpectedly low absorption of light within the turbid medium. This dielectric relaxation time of deionized, purified, water has been found to be approximately 250 femtoseconds (fs) at some wavelengths of light, while impure water as found in many turbid media having a significant aqueous component may have shorter relaxation times. In particular, it has been found that, in most turbid media having a significant aqueous component such as fog, clouds, turbid water including seawater, human and animal tissue, and milk, some reduction in absorption and scattering, and a substantial reduction in absorption and scattering occurs with laser pulse widths of 60 fs or less; reduction in absorption and scattering is accompanied by an increase in mean free path.

The exact values of the relaxation time vary somewhat with the turbid medium, and are wavelength dependent. Further, some interactions of photons with scattering particles are known to be wavelength and particle size dependent.

Figure 1:
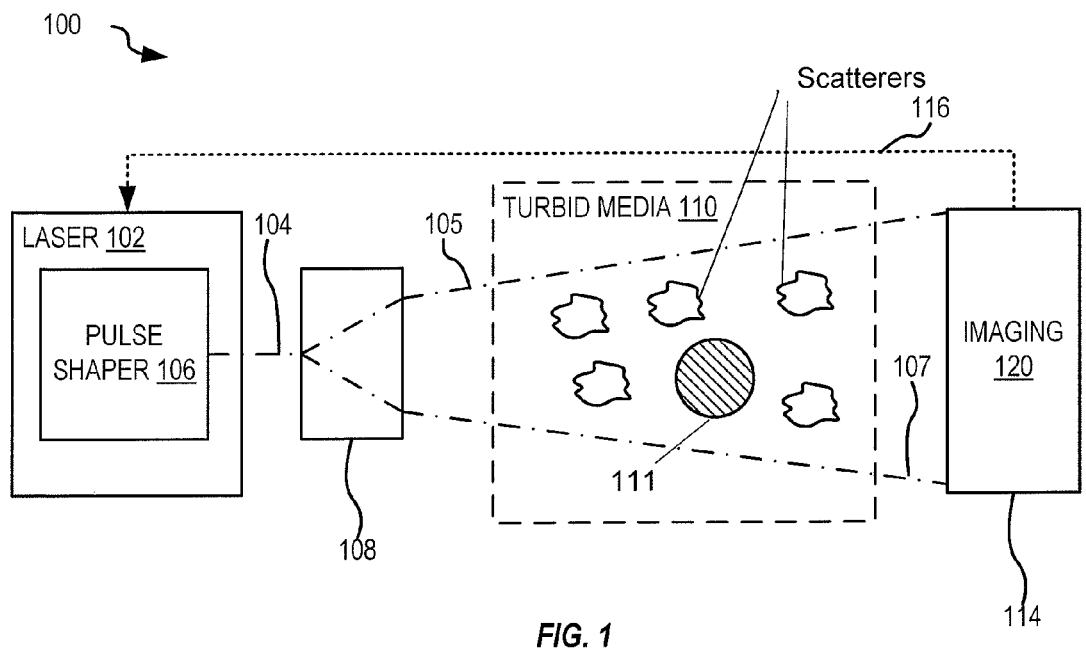
FIG. 1 shows one exemplary system embodiment for imaging through turbid media.

FIG. 1 shows one exemplary system 100 for imaging through turbid media 110. Turbid media 110 is for example soil, turbid water, biological tissue, clouds, fog, or other non-homogeneous media having a tendency to scatter light; however, it will be understood that system 100 may provide enhanced imaging through any number of turbid media. A laser 102 generates a repetitive pulsed light beam 104 under control of a pulse shaper 106. Light beam 104 enters a diverging device 108 that increases the cross-sectional area of beam 104. In one example, diverging device 108 is formed of optical lenses. In another example, diverging device 108 is a scanning device that causes beam 104 to scan an increased area. Diverging device 108 serves to help prevent the beam power density low enough to avoid nonlinear interactions such as thermal blooming caused by localized heating of portions of turbid medium 110. In yet another embodiment, beam power density is kept low such that nonlinear interactions are avoided by keeping pulse width sufficiently narrow and pulse repetition rate low enough that thermal blooming is avoided. In one example of operation, pulsed beam 104 increases in cross-sectional area to form a diverged or scanned pulsed beam 105. Diverged or scanned pulsed beam 105 propagates through turbid media 110 to form beams 107.

Within turbid medium 110 may be an object of interest 111 such as bones, bullets, tumors, stones, vehicles, soldiers, ships etc. of which an image is desired The light beams emerge from the turbid media 110 having three components —ballistic, diffusive, and snake photons that are processed and imaged.

In addition to the base medium component and the scattering particles, there may be an object of interest located within the medium By shaping pulses from laser 102, such that the beam has pulse width of less than a relaxation time of the turbid medium 110, pulsed beam 105 passes through turbid media 110 with reduced absorption and scattering, thereby reducing the intensity of scattered photons and producing improved imagery 120 by increasing the intensity of ballistic and snake photons received by the sensor 114. Attenuation of beam 105 through turbid media is for example reduced by optimizing temporal pulse width, pulse repetition rate and/or chirp of each pulse, yielding beams 107 with increased signal-to-noise ratios for detection at sensor 114.

In some embodiments, a feedback signal 116 connects sensor 114 and pulse shaper 106, such that pulse shaper 106 may selectively modify width, frequency, repetition rate and chirp of beam 104 to optimize propagation of beam 105 through turbid media 110. In one embodiment, pulse shaper 106 automatically optimizes frequency, pulse width, repetition rate and chirp of pulses generated by laser 102 to optimize imagery 120 as sensed by sensor 114.

In another embodiment, pulse shaper 106 uses a predetermined set of parameters to set wavelength, pulse width, repetition rate, and chirp of pulses generated by laser 102 to values expected to provide adequate performance, including a pulse width less than the expected relaxation time of the turbid medium. In an embodiment for use with turbid media having a significant aqueous component such as fog or murky water, this pulse width is less than 240 fs and preferably 60 fs or less.

In another embodiment resembling that of FIG. 1, after pulse shaper 106 has set a baseline wavelength, pulse width, repetition rate, and chirp for minimum pulse attenuation and scattering, one or more of these parameters, or pulse intensity, of laser 102 is further modulated by pulse shaper 106 as known in the art with a message. In this embodiment, sensor 114 incorporates a demodulator for recovering the message from the modulated laser beam 105. The system then becomes a system for conveying messages through the turbid medium.

Figure 2:
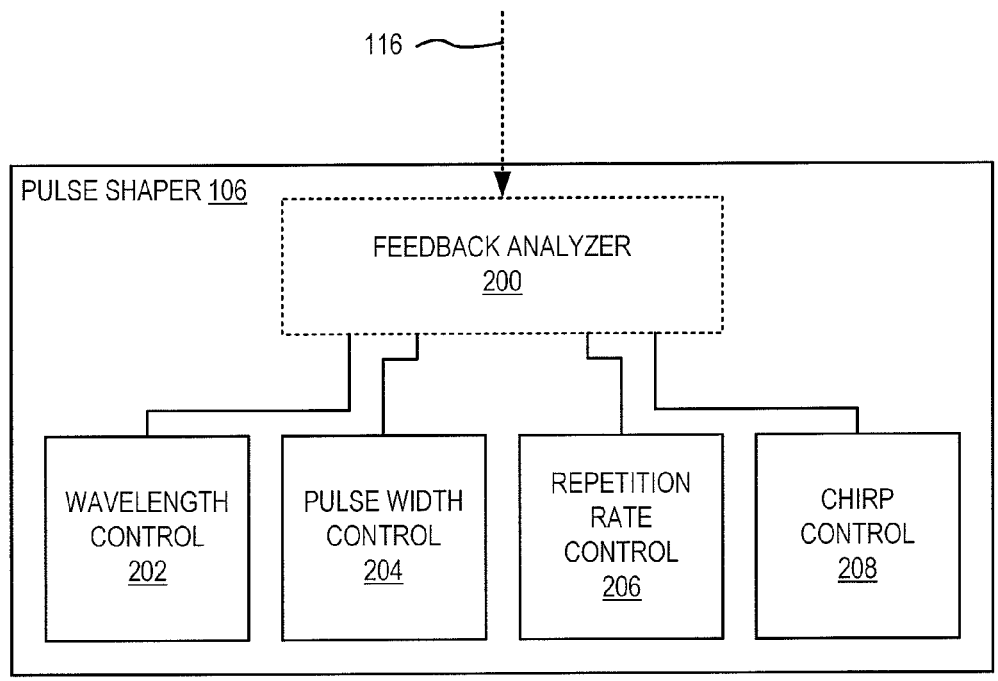
FIG. 2 shows a pulse shaper including an optional feedback analyzer, a frequency control, a pulse width control, a repetition rate control and a chirp control.

FIG. 2 shows pulse shaper 106 of FIG. 1 including an optional feedback analyzer 200, a frequency control 202, a pulse width control 204, a repetition rate control 206 and a chirp control 208. Wavelength control 202 controls the fundamental frequency or wavelength of light output from laser 102. Pulse width control 204 controls the width of the pulses of light output from laser 102. Repetition rate control 206 controls the interval between pulses output by laser 102. Chirp control 208 controls the chirp of each pulse output by laser 102. For example, chirp control 208 may control laser 102 to generate pulses with 'up-chirp' if propagation through turbid media 110 improves with up-chirp. Alternatively, chirp control 208 may control laser 102 to generate pulses with 'down-chirp' if propagation of beam 105 through turbid media 110 improves with down-chirp.

Feedback analyzer 200, if included, receives input from sensor 114 through feedback signal 116. Feedback analyzer 200, based upon feedback from sensor 114, determines optimum settings for frequency control 202, pulse width control 204, repetition rate control 206 and chirp control 208 to produce optimum imagery of an object within turbid media 110 from sensor 114.

In a particular embodiment feedback analyzer repeatedly determines an image quality of imagery 120 received by the sensor 114 by, for example, performing a 2-d fourier transform of the image. The feedback analyzer then selects a parameter selected from the group including pulse wavelength, pulse width, pulse rate, and chirp characteristics. It then repeatedly adjusts the selected parameter until an optimum value, a value of that parameter producing the best quality image is found. The analyzer then selects another parameter from the group and optimizes it in succession. Once all parameters are optimized, an image is obtained. System 100 is for example a self-tuning system that dynamically and automatically shapes pulses with pulse shaper 106, based upon image quality at sensor 114.

It is believed that optimization of pulse wavelength and pulse width together offer the greatest opportunities to optimize image quality, and that best results will be obtained with pulse widths of less than the dielectric relaxation time of the turbid media, typically less than 240 fs.

Figure 3:
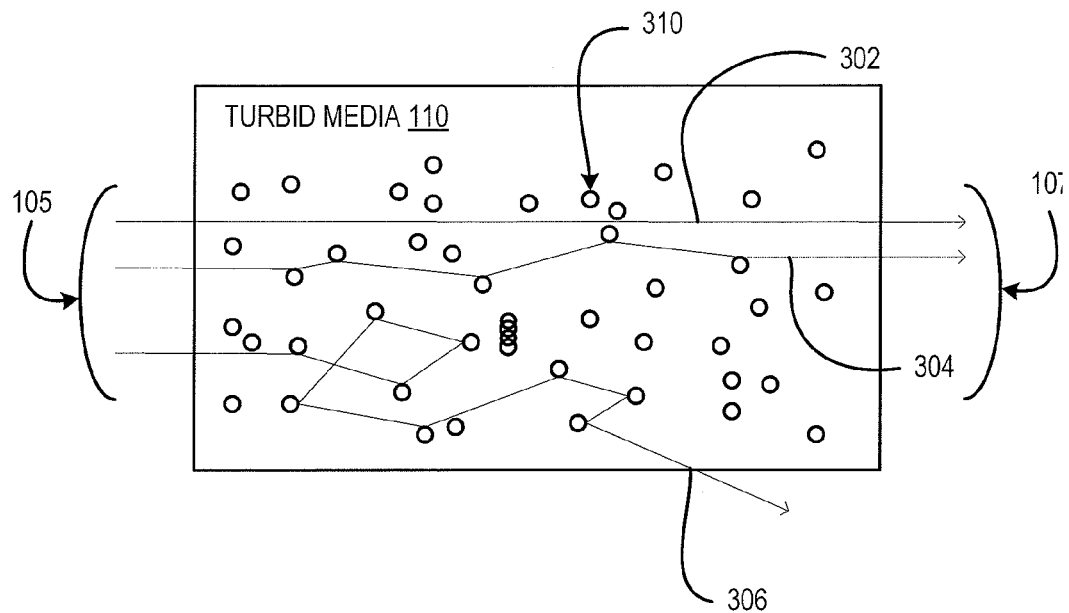
FIG. 3 shows a light beam scattering within a turbid medium.

FIG. 3 shows light beam 105 scattering in turbid medium 110. Turbid Medium 110 is a medium typically having a base medium component and random aggregate scatterers 310. While some photons may penetrate unaltered, many photons undergo scattering; such that the light beam 107 emerging from turbid medium 110 has three components: ballistic photons 302, snake photons 304, and diffusive photons 306. These components differ in their paths through turbid medium 110 and consequently in their imaging properties. The ballistic photons 302 and snake photons 304, having the shortest trajectories through turbid medium 110, travel unscattered or forward scattered thus emerging at beam 107 first. These photons preserve the characteristics of the incident light, namely direction of propagation and polarization, and are hence best for imaging.

Figure 4:
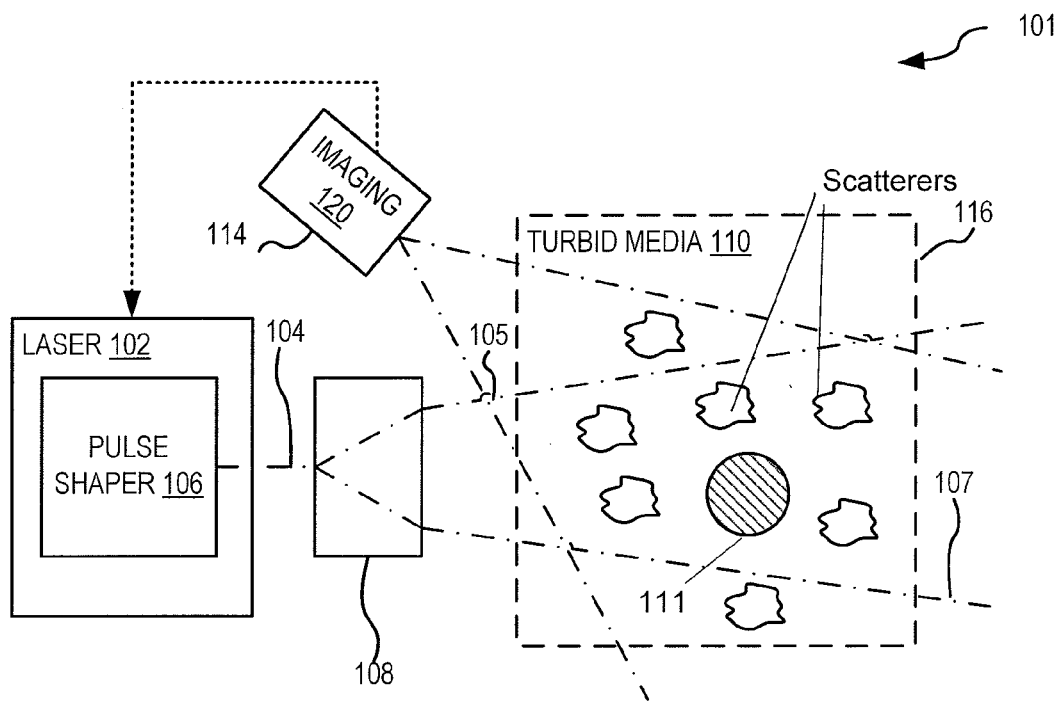
FIG. 4 shows the light beam of FIG. 3 entering a imaging device <whack>.

FIG. 4 illustrates an alternative embodiment of the system of FIG. 1, optimized for imaging by reflected photons instead of by transmission. In the embodiment of FIG. 4, the laser 102 and sensor 114 may be located on the same side of turbid medium 110. In an exemplary system 101 for imaging through turbid media 110, a laser 102 generates a repetitive pulsed light beam 104 under control of a pulse shaper 106. Light beam 104 enters a diverging device 108 that increases the cross-sectional area of beam 104. In one example, diverging device 108 is formed of optical lenses. In another example, diverging device 108 is a scanning device that causes beam 104 to scan an increased area. In yet another embodiment, beam power density is kept low that nonlinear interactions are avoided by keeping pulse width sufficiently narrow and pulse repetition rate low enough that thermal blooming is avoided. In one example of operation, pulsed beam 104 increases in cross-sectional area to form a diverged or scanned pulsed beam 105. Diverged or scanned pulsed beam 105 propagates through turbid media 110 as beams 107.

Within turbid medium 110 may be an object of interest 111 such as bones, bullets, tumors, stones, vehicles, soldiers, ships etc. of which an image is desired. The light beams interact with the object of interest 111, and some are reflected by the object of interest. Photons, including diffusive photons from the incident laser 102 source, and reflected photons from the object of interest 111, emerge from the turbid media 110 having three components—ballistic, diffusive, and snake photons that are processed and imaged.

By shaping pulses from laser 102, such that the beam has pulse width of less than a relaxation time of the turbid medium 110, pulsed beam 105 passes through turbid media 110 with reduced absorption and scattering, thereby reducing the intensity of scattered photons and producing improved imagery 120 from sensor 114 by increasing the intensity of ballistic and snake photons received by the sensor 114. Attenuation of beam 105 through turbid media is for example reduced by optimizing temporal pulse width, pulse repetition rate and/or chirp of each pulse, yielding beams 107 with increased signal-to-noise ratios for detection at sensor 114.

In some embodiments, feedback signal 116 connects sensor 114 and pulse shaper 106, such that pulse shaper 106 may selectively modify width, frequency, repetition rate and chirp of beam 104 to optimize propagation of beam 105 through turbid media 110. In one embodiment, pulse shaper 106 automatically optimizes frequency, pulse width, repetition rate and chirp of pulses generated by laser 102 to optimize imagery 120 as sensed by sensor 114.

In another embodiment, pulse shaper 106 uses a predetermined set of parameters to set wavelength, pulse width, repetition rate, and chirp of pulses generated by laser 102 to values expected to provide adequate performance, including a pulse width less than the expected relaxation time of the turbid medium. In an embodiment for use with turbid media having a significant aqueous component, this pulse width is less than 240 fs and preferably 60 fs or less.

Figure 5:
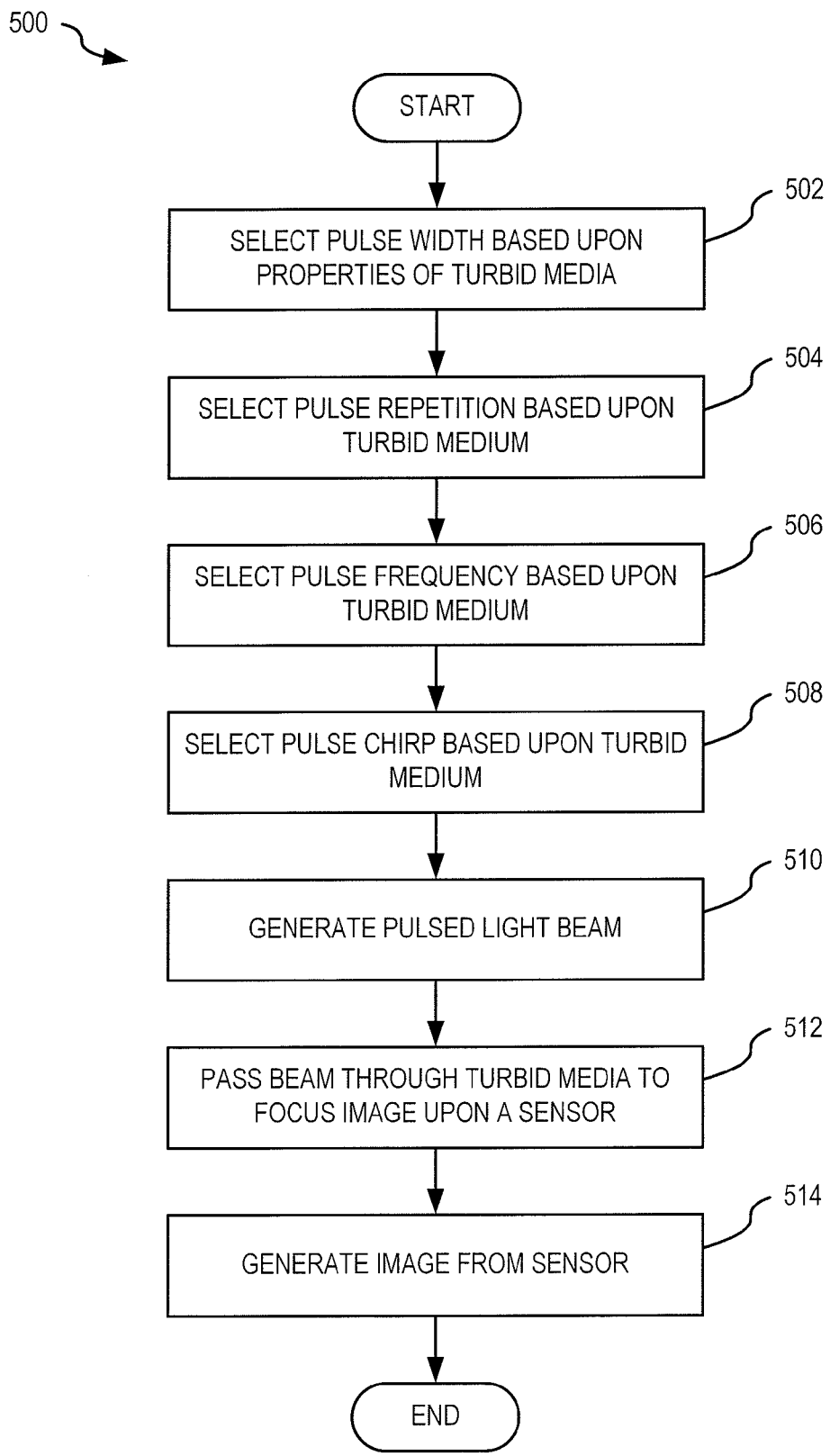
FIG. 5 is a flowchart illustrating one exemplary method for imaging through turbid media.

FIG. 5 is a flowchart illustrating one exemplary method 500 for imaging in turbid media. In step 502, a pulse width is selected based upon the properties of the turbid media to be imaged. In one example of step 502, pulse width control 204 within pulse shaper 106 is set to control laser 102 to produce pulses of appropriate width for propagating through turbid media 110. In step 504, a pulse repetition rate is selected based upon the properties of the turbid media to be imaged. In some embodiments these parameters are selected from a table of parameters according to anticipated media characteristics, typically including a pulse width of less than 240 fs and in some embodiments less than 60 ps. In other embodiments these parameters are found by searching for parameters producing the best image under prevailing conditions at the moment. For example, particle size and particle density of fog may vary from day to day, where some incremental image improvement may be obtained by searching for optimum parameters that fit the current fog, not those determined for a previous fog.

In one example of step 504, repetition rate control 206 within pulse shaper 106 is set to control laser 102 to produce pulses with an appropriate repetition rate for propagating through turbid media 110. In step 506, pulse wavelength is selected based upon properties of the turbid media to be imaged. In one example of step 506, wavelength control 202 within pulse shaper 106 is set to control laser 102 to produce pulses with an appropriate wavelength for propagating through turbid media 110. In step 508, pulse chirp is selected based upon the properties of the turbid media to be imaged. In one example of step 508, chirp control 208 within pulse shaper 106 is set to control laser 102 to produce pulses with an appropriate chirp for propagating through turbid media 110.

In step 510, a pulsed light beam is generated. In one example of step 510, pulse shaper 106 controls laser 102 to produce pulsed light beam 104. In step 512, the light beam is passed through the turbid media to focus an image upon a sensor. In one example of step 512, light beam 104 is diverged by a diverging device 108 to produce beam 105 which is passed through turbid media 110 and then upon sensor 114. In step 514, an image of the objects of interest 111 is generated from information received by the sensor. In one example of step 514, an image of the objects of interest 111 is generated from sensor 114 data derived from incident light from beam 105 after beam 105 passes through turbid media 110. Steps within method 500 may be implemented in an alternate order without departing from the scope hereof.

Figure 6:
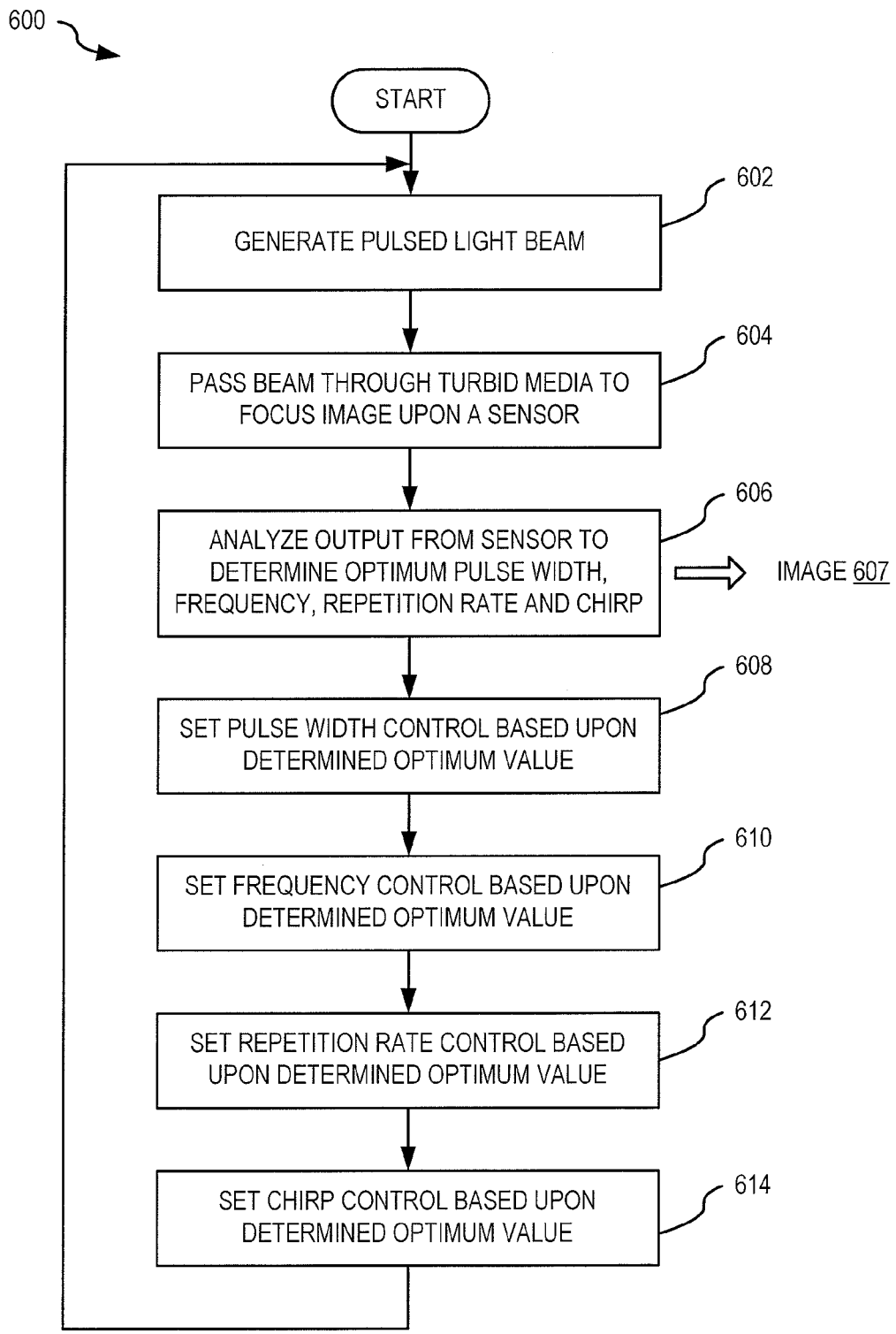
FIG. 6 is a flowchart illustrating one exemplary method for imaging through turbid media.

FIG. 6 is a flowchart illustrating one exemplary method for imaging through turbid media. In step 602, a pulsed light beam is generated. In one example of step 602, pulse shaper 106 controls laser 102 to generate pulsed light beam 104. In step 604, the beam is passed through turbid media to project an image of the objects of interest 111 upon a sensor. In one example of step 604, pulsed light beam 104 passes through diverging device 108 to form beam 105 which then passes through turbid media 110 and forms an image on sensor 114. In step 606, output from sensor is analyzed to determine optimum pulse width, wavelength, repetition rate and chirp. In one example of step 606, feedback analyzer 200 receives output from sensor 114 and determines optimum settings for wavelength control 202, pulse width control 204, repetition rate control 206 and chirp control 208, to enhance quality of an image 607. In step 608, pulse width control is set to the determined optimum value. In one example of step 608, width control 204 adjusts width of pulses output from pulse shaper 106, according to optimum settings determined by feedback analyzer 200. In step 610, wavelength control is set based upon the optimum value determined at feedback analyzer 200. Wavelength control 202 for example adjusts wavelength of light output from pulse shaper 106, to the determined optimum value. Repetition rate control is adjusted based upon the determined optimum value, for example by repetition rate control 206, in step 612. In step 614, chirp control is set based upon the determined optimum value. Pulse shaper 106 for example employs chirp control 208 to generate pulses with up-chirp or down-chirp if information from feedback analyzer 200 indicates that propagation of the light beam improves with up-chirp or down-chirp.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A method for imaging objects through turbid media comprising:
   generating a repetitive pulsed light beam at a first wavelength under control of a pulse shaper, the pulses having a chirp determined to increase quality of captured image;
   propagating said light beam through turbid media;
   receiving the light beam at a sensor adapted to detect light at the first wavelength;
   imaging the received light beam with the sensor; and
   optimizing the chirp to increase quality of the captured image;
   wherein the pulsed light beam has a pulse width of less than 240 femtoseconds.

2. The method of claim 1, wherein the pulsed light beam has a pulse width of less than 60 femtoseconds.

3. The method of claim 1, further comprising automatically optimizing a parameter selected from the group consisting of pulse width, wavelength, and repetition rate of said light beam for best image quality.

4. The method of claim 1, further comprising increasing cross-sectional area of the light beam with a diverging device, prior to propagating the light beam through the turbid media.

5. The method of claim 1, wherein the sensor does not attempt to separate ballistic from diffusive photons based upon time differences between these photons.

6. The method of claim 1, wherein the sensor and a laser for generating the pulsed light beam are located on the same side of the turbid medium.

7. A system for imaging objects through turbid media comprising:
   a laser for generating a light beam;
   a pulse shaper comprising a feedback analyzer for receiving a feedback signal, the pulse shaper configured to control said light beam by setting at least pulse wavelength and pulse width to values determined to provide minimum attenuation and scattering in the turbid medium, and further comprising a chirp control in communication with the feedback analyzer, the chirp control selectively modifying the chirp of the pulses of the light beam, to increase quality of captured image; and
   a sensor, in communication with the pulse shaper, for detecting said light beam through a turbid medium;
   wherein the light beam comprises pulses of pulse width less than 250 femtoseconds.

8. A system of claim 7, wherein the light beam comprises pulses of pulse width less than 60 femtoseconds.

9. A system of claim 7, the sensor comprising an imaging device and located on a same side of the turbid medium as the laser.

10. A system of claim 9, wherein the sensor communicates with the pulse shaper via a feedback signal, to automatically optimize at least one parameter of the light beam selected from the group consisting of pulse width, wavelength, repetition rate and chirp.

11. The system of claim 10, the pulse shaper comprising a wavelength control in communication with the feedback analyzer, for selectively modifying the wavelength of the light beam to increase quality of the captured image.

12. The system of claim 11, the pulse shaper comprising a pulse width control in communication with the feedback analyzer, for selectively modifying the pulse width of the light beam to increase quality of the captured image.

13. The system of claim 12, the pulse shaper comprising a repetition rate control in communication with the feedback analyzer, for selectively modifying a pulse rate of the light beam, to increase quality of the captured image.

14. A system for imaging objects through turbid media comprising:
   a laser for generating a light beam;
   a pulse shaper for controlling said light beam by setting at least pulse wavelength and pulse width to values determined to provide minimum attenuation and scattering in the turbid medium; and
   a sensor comprising an imaging device and located on a same side of the turbid medium as the laser, the sensor in communication with the pulse shaper, and configured for detecting said light beam received through a turbid medium;

wherein the light beam comprises pulses of pulse width less than 250 femtoseconds;

wherein the sensor communicates with the pulse shaper via a feedback signal, to automatically optimize at least one parameter of the light beam selected from the group consisting of pulse width, wavelength, repetition rate and chirp, and wherein the pulse shaper comprises a feedback analyzer for receiving the feedback signal; and a wavelength control in communication with the feedback analyzer, the wavelength control for selectively modifying the wavelength of the light beam to increase quality of captured image;

the pulse shaper further comprising a pulse width control in communication with the feedback analyzer, for selectively modifying the pulse width of the light beam to increase quality of the captured image; and the pulse shaper controlling emission of the light beam in pulses and further comprising a chirp control in communication with the feedback analyzer, the chirp control selectively modifying the chirp of the pulsed beam, to increase quality of the captured image.

* * * * *